US008540452B2

(12) United States Patent
Jimenez et al.

(10) Patent No.: US 8,540,452 B2
(45) Date of Patent: Sep. 24, 2013

(54) FLEXIBLE JOINT ARRANGEMENT INCORPORATING FLEXURE MEMBERS

(75) Inventors: Omar F. Jimenez, Gering, NE (US); Nicholas Ransom Powley, St. Paul, MN (US)

(73) Assignee: Spinex Tec, LLC, Gering, NE (US)

( * ) Notice: Subject to any disclaimer, the term of this patent is extended or adjusted under 35 U.S.C. 154(b) by 179 days.

(21) Appl. No.: 12/651,266

(22) Filed: Dec. 31, 2009

(65) Prior Publication Data
US 2010/0209184 A1    Aug. 19, 2010

Related U.S. Application Data

(60) Provisional application No. 61/142,104, filed on Dec. 31, 2008, provisional application No. 61/291,203, filed on Dec. 30, 2009.

(51) Int. Cl.
*F16C 11/04* (2006.01)

(52) U.S. Cl.
USPC ........................................ 403/220; 623/17.16

(58) Field of Classification Search
USPC ........ 403/220, 291; 16/225, 226; 623/17.11, 623/17.13, 17.15, 17.16; 606/246, 90
See application file for complete search history.

(56) References Cited

U.S. PATENT DOCUMENTS

| | | | |
|---|---|---|---|
| 2,106,088 A | 1/1938 | De Tar |
| 2,231,221 A | 2/1941 | Rector |
| 2,453,656 A | 11/1948 | Bullard |
| 2,666,334 A | 1/1954 | Nalle |
| 2,711,105 A | 6/1955 | Williams |
| 2,842,976 A | 7/1958 | Young |
| 3,386,128 A | 6/1968 | Vyvyan |
| 3,449,971 A | 6/1969 | Posh |

(Continued)

FOREIGN PATENT DOCUMENTS

| | | |
|---|---|---|
| EP | 1342456 | 9/2003 |
| EP | 1552797 A2 | 7/2005 |

(Continued)

OTHER PUBLICATIONS

International Search Report and Written Opinion of the International Searching Authority or the Declaration dated Sep. 27, 2010, International Application No. PCT/US2009/069876, filed Dec. 30, 2009, 12 pages.

(Continued)

*Primary Examiner* — Michael P Ferguson
*Assistant Examiner* — Daniel Wiley
(74) *Attorney, Agent, or Firm* — Patterson Thuente Pedersen, P.A.

(57) ABSTRACT

Flexible joint arrangements employ at least one flexure member that interfaces with wrapping surfaces defined on the bases to which the ends of the flexure member are connected. The flexure members are configured to define a traveling instantaneous axis of rotation that moves along a path defined by the interface of the flexure and the wrapping surfaces as the bases move relative to each other. The flexure members and the bases can be constructed of a monolithic material. The wrapping surfaces of the bases can be asymmetric in cross-sectional shape. The radius of curvature of the traveling instantaneous axis of rotation can be configured to change only in discrete quantum steps without reversals. The flexible joint arrangement can be configured as one or more three bar linkages in which the middle bar is rigid and the outer bars are flexure members in accordance with the various embodiments.

6 Claims, 9 Drawing Sheets

(56) References Cited

U.S. PATENT DOCUMENTS

| | | | |
|---|---|---|---|
| 3,575,475 A * | 4/1971 | Boerner | 403/291 |
| 3,596,863 A | 8/1971 | Kaspareck | |
| 3,597,938 A * | 8/1971 | Hellen et al. | 464/78 |
| 3,700,289 A * | 10/1972 | Bilinski et al. | 403/291 |
| 3,700,290 A * | 10/1972 | Ensinger | 403/291 |
| 3,708,925 A | 1/1973 | Ainoura | |
| 3,709,132 A | 1/1973 | Farrell | |
| 3,916,596 A | 11/1975 | Hawley | |
| 3,985,000 A * | 10/1976 | Hartz | 464/99 |
| 3,988,906 A * | 11/1976 | Smith | 464/88 |
| 4,261,211 A | 4/1981 | Haberland | |
| 4,478,109 A | 10/1984 | Kobelt | |
| 4,528,864 A | 7/1985 | Craig | |
| 4,559,717 A | 12/1985 | Scire | |
| 4,630,495 A | 12/1986 | Smith | |
| 4,691,586 A | 9/1987 | Van Leijenhorst | |
| 4,694,703 A | 9/1987 | Routson | |
| 4,869,552 A | 9/1989 | Tolleson | |
| 5,133,108 A | 7/1992 | Esnault | |
| 5,181,371 A | 1/1993 | Deworth | |
| 5,196,857 A | 3/1993 | Chiappetta | |
| 5,198,932 A | 3/1993 | Takamura | |
| 5,374,556 A | 12/1994 | Bennett | |
| 5,439,377 A | 8/1995 | Milanovich | |
| 5,445,471 A * | 8/1995 | Wexler et al. | 403/220 |
| 5,645,599 A | 7/1997 | Samani | |
| 5,664,457 A | 9/1997 | Nejati | |
| 5,904,479 A | 5/1999 | Staples | |
| 5,960,670 A | 10/1999 | Iverson | |
| 5,980,252 A | 11/1999 | Samchukov | |
| 5,988,006 A | 11/1999 | Fleytman | |
| 6,045,579 A | 4/2000 | Hochshuler | |
| 6,056,491 A | 5/2000 | Hsu | |
| 6,136,031 A * | 10/2000 | Middleton | 623/17.16 |
| 6,175,989 B1 | 1/2001 | Carpenter | |
| 6,315,797 B1 * | 11/2001 | Middleton | 623/17.16 |
| 6,350,317 B1 | 2/2002 | Hao et al. | |
| 6,378,172 B1 | 4/2002 | Schrage | |
| 6,395,035 B2 * | 5/2002 | Bresina et al. | 623/17.15 |
| 6,454,806 B1 | 9/2002 | Cohen | |
| 6,484,608 B1 | 11/2002 | Ziavras | |
| 6,517,772 B1 | 2/2003 | Woolf | |
| 6,554,526 B1 * | 4/2003 | Egelandsdal | 403/294 |
| 6,719,796 B2 | 4/2004 | Cohen | |
| 6,772,479 B2 | 8/2004 | Hinkley | |
| 6,802,229 B1 | 10/2004 | Lambert | |
| 6,808,537 B2 | 10/2004 | Michelson | |
| 6,932,844 B2 * | 8/2005 | Ralph et al. | 623/17.16 |
| 6,953,477 B2 | 10/2005 | Berry | |
| 7,018,415 B1 | 3/2006 | McKay | |
| 7,051,610 B2 | 5/2006 | Stoianovici | |
| 7,070,598 B2 | 7/2006 | Lim | |
| 7,201,751 B2 | 4/2007 | Zucherman | |
| 7,273,373 B2 | 9/2007 | Horiuchi | |
| 7,308,747 B2 | 12/2007 | Smith | |
| 7,316,381 B2 | 1/2008 | Hacker | |
| 7,410,201 B1 | 8/2008 | Wilson | |
| 7,425,103 B2 | 9/2008 | Perez-Sanchez | |
| 7,435,032 B1 | 10/2008 | Murphey | |
| 7,584,682 B2 | 9/2009 | Hsiao | |
| 7,611,538 B2 * | 11/2009 | Belliard et al. | 623/17.15 |
| 7,674,296 B2 * | 3/2010 | Rhoda et al. | 623/17.15 |
| 7,682,376 B2 | 3/2010 | Trieu | |
| 7,753,958 B2 | 7/2010 | Gordon et al. | |
| 7,758,645 B2 * | 7/2010 | Studer | 623/17.13 |
| 7,892,285 B2 * | 2/2011 | Viker | 623/17.13 |
| 7,896,919 B2 * | 3/2011 | Belliard et al. | 623/17.15 |
| 7,947,078 B2 * | 5/2011 | Siegal | 623/17.11 |
| 2003/0077110 A1 | 4/2003 | Knowles | |
| 2003/0233145 A1 | 12/2003 | Landry | |
| 2004/0111157 A1 * | 6/2004 | Ralph et al. | 623/17.13 |
| 2004/0225364 A1 | 11/2004 | Richelsoph et al. | |
| 2005/0000228 A1 | 1/2005 | De Sousa | |
| 2005/0033431 A1 | 2/2005 | Gordon | |
| 2005/0095384 A1 * | 5/2005 | Wittmeyer, Jr. | 428/40.1 |
| 2005/0113924 A1 | 5/2005 | Buttermann | |
| 2005/0175406 A1 | 8/2005 | Perez-Sanchez | |
| 2006/0004447 A1 | 1/2006 | Mastrorio | |
| 2006/0004455 A1 | 1/2006 | Leonard | |
| 2006/0025862 A1 | 2/2006 | Villiers et al. | |
| 2006/0129244 A1 | 6/2006 | Ensign | |
| 2006/0149385 A1 | 7/2006 | McKay | |
| 2006/0184171 A1 | 8/2006 | Biedermann | |
| 2006/0247781 A1 * | 11/2006 | Francis | 623/17.16 |
| 2006/0293752 A1 * | 12/2006 | Moumene et al. | 623/17.13 |
| 2007/0032791 A1 | 2/2007 | Greenhalgh | |
| 2007/0049943 A1 | 3/2007 | Moskowitz | |
| 2007/0083267 A1 * | 4/2007 | Miz et al. | 623/17.13 |
| 2007/0129730 A1 | 6/2007 | Woods et al. | |
| 2007/0185577 A1 | 8/2007 | Malek | |
| 2007/0191954 A1 | 8/2007 | Hansell | |
| 2007/0191958 A1 | 8/2007 | Abdou | |
| 2007/0219634 A1 * | 9/2007 | Greenhalgh et al. | 623/17.16 |
| 2007/0222100 A1 | 9/2007 | Husted | |
| 2007/0282449 A1 | 12/2007 | de Villiers et al. | |
| 2007/0293329 A1 | 12/2007 | Glimpel | |
| 2007/0293948 A1 | 12/2007 | Bagga | |
| 2008/0026903 A1 | 1/2008 | Flugrad | |
| 2008/0077246 A1 * | 3/2008 | Fehling et al. | 623/17.16 |
| 2008/0100179 A1 | 5/2008 | Ruggeri et al. | |
| 2008/0161920 A1 * | 7/2008 | Melkent | 623/17.11 |
| 2008/0161931 A1 * | 7/2008 | Perez-Cruet et al. | 623/17.16 |
| 2008/0168855 A1 | 7/2008 | Giefer | |
| 2008/0188941 A1 | 8/2008 | Grotz | |
| 2008/0210039 A1 | 9/2008 | Brun | |
| 2008/0221694 A1 | 9/2008 | Warnick | |
| 2008/0234736 A1 * | 9/2008 | Trieu et al. | 606/250 |
| 2008/0281423 A1 * | 11/2008 | Sheffer et al. | 623/17.11 |
| 2008/0292293 A1 * | 11/2008 | Voellmer | 403/220 |
| 2008/0319487 A1 * | 12/2008 | Fielding et al. | 606/263 |
| 2009/0012564 A1 | 1/2009 | Chirico | |
| 2009/0076614 A1 * | 3/2009 | Arramon | 623/17.16 |
| 2009/0164017 A1 | 6/2009 | Sommerich | |
| 2009/0222169 A1 * | 9/2009 | Cipoletti et al. | 623/17.16 |
| 2010/0004688 A1 * | 1/2010 | Maas et al. | 606/248 |
| 2010/0082109 A1 * | 4/2010 | Greenhalgh et al. | 623/17.15 |
| 2010/0094305 A1 | 4/2010 | Chang | |
| 2010/0185291 A1 * | 7/2010 | Jimenez et al. | 623/17.16 |
| 2010/0209184 A1 | 8/2010 | Jimenez et al. | |
| 2011/0093075 A1 * | 4/2011 | Duplessis et al. | 623/17.16 |
| 2011/0112644 A1 * | 5/2011 | Zilberstein et al. | 623/17.15 |

FOREIGN PATENT DOCUMENTS

| | | |
|---|---|---|
| EP | 1881209 | 10/2008 |
| JP | 05-81194 | 11/1993 |
| JP | 2004-301135 | 10/2004 |
| JP | 2008-208932 | 9/2008 |
| WO | WO 2004/026188 | 4/2004 |
| WO | WO2004/109155 | 12/2004 |
| WO | WO 2005/081330 | 9/2005 |
| WO | WO 2005/096975 A2 | 10/2005 |
| WO | WO 2006/094535 | 9/2006 |
| WO | WO 2006/116052 | 11/2006 |
| WO | WO 2006/125329 | 11/2006 |
| WO | WO 2007/002583 | 1/2007 |
| WO | WO 2007/009107 A2 | 1/2007 |
| WO | WO 2007/028140 | 3/2007 |
| WO | WO 2007/076377 A2 | 7/2007 |
| WO | WO 2008/137192 | 11/2008 |
| WO | WO 2009/018349 | 2/2009 |
| WO | WO 2010/078520 | 12/2009 |

OTHER PUBLICATIONS

International Search Report and Written Opinion of the International Searching Authority or the Declaration dated Nov. 29, 2010, International Application No. PCT/US2009/069958, filed Dec. 31, 2009, 9 pages.

Wenzel Spine, Inc., *VariLift® -L Expandable Interbody Fusion Device: A proven solution for stand-alone fusion*, Product Overview, 12 pages, © 2010.

Peter A. Halverson, et. al., Tension-based Multi-stable Compliant Rolling-contact Elements, Department of Mechanical Engineering, Brigham Young University, Provo UT, USA 84602 (34 pages), 2007.

Just L. Herder, Force Directed Design of Laparoscopic Forceps, 1998, ASME Design Engineering Technical Conference (8 pages).

Alexander H. Slocum, Fundamentals of Design (2005).

Amelie Jeanneau, et. al., A Compliant Rolling Contact Joint and its Application in a 3-DOF Planar Parallel Mechanism with Kinematic Analysis, ASME (2004) Design Engineering Technical Conferences (9 pages).

Application and File History of U.S. Appl. No. 12/650,994, Inventors Jimenez et al., filed Dec. 31, 2009.

Application and File History of U.S. Appl. No. 12/407,608, Inventors Omar F. Jimenez, filed Mar. 19, 2009.

Application and File History of U.S. Appl. No. 12/841,465, Inventors Jimenez et al., filed Jul. 22, 2010.

Application and File History of U.S. Appl. No. 12/841,869, Inventors Jimenez et al., filed Jul. 22, 2010.

W. Küsswetter, *A Supplementary Instrumentation for Posterior Fusion of Spine in Scoliosis*, Archives of Orthopedic Traumatic Surgery, 1980, 1 page.

Chou et al., *Efficacy of Anterior Cervical Fusion: Comparison of Titanium Cages*, polyetheretherketone (*PEEK*) *cages and autogenous bone grafts*, Journal of Clinical Neuroscience, 2008, pp. 1240-1245.

Hunter et al., *Overview of Medical Devices*, Department of Radiology, University of Arizona, Aug. 2001, pp. 89-140, vol. 30, No. 4, ISSN: 0363-0188.

Notification of Transmittal of the International Search Report and the Written Opinion of the International Searching Authority or the Declaration, Application No. PCT/US2010/042941, mailed Apr. 25, 2011.

International Search Report, Application No. PCT/US2010/042915, mailed Apr. 22, 2011.

Application No. PCT/US2009/069958, *Notification Concerning Transmittal of International Preliminary Report on Patentability*, mailed Jul. 14, 2011, 4 pages.

Application No. PCT/US2009/069876, Notification Concerning Transmittal of International Preliminary Report on Patentability, mailed Jul. 14, 2011, 7 pages.

European Application No. EP 09837185, European Search Report dated May 14, 2013, 7 pages.

\* cited by examiner

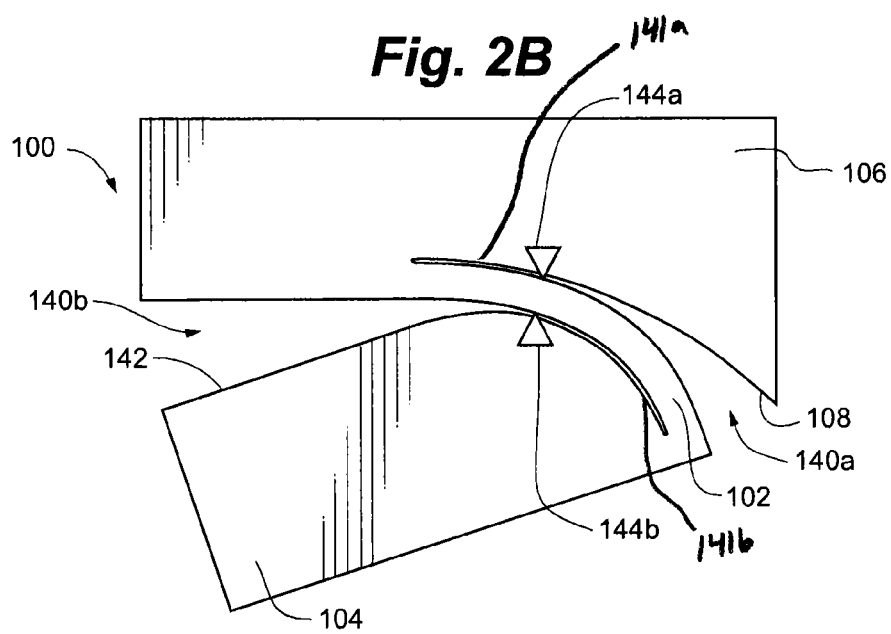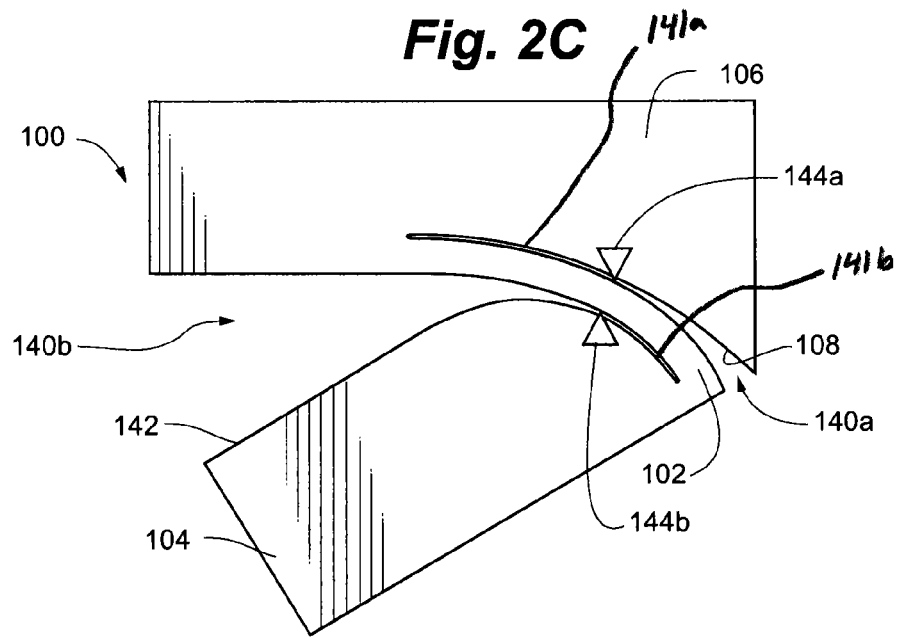

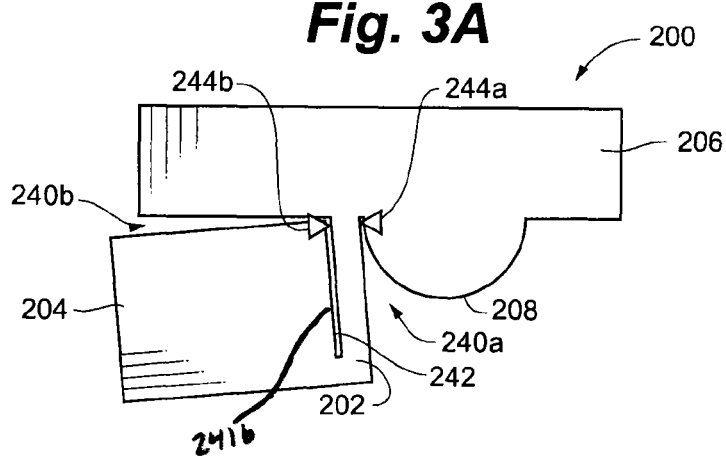
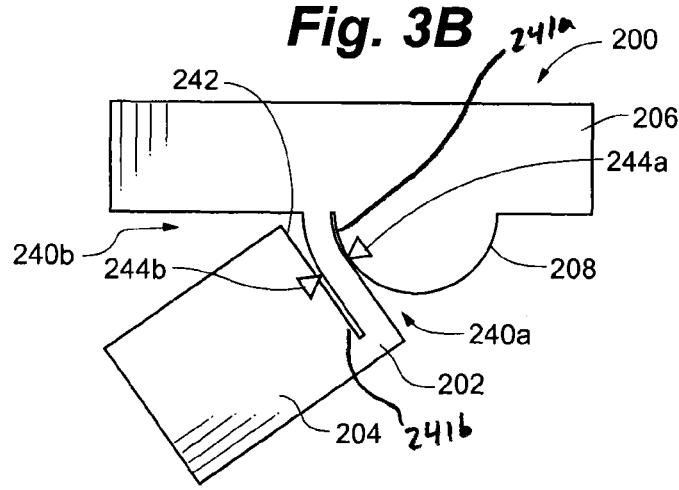
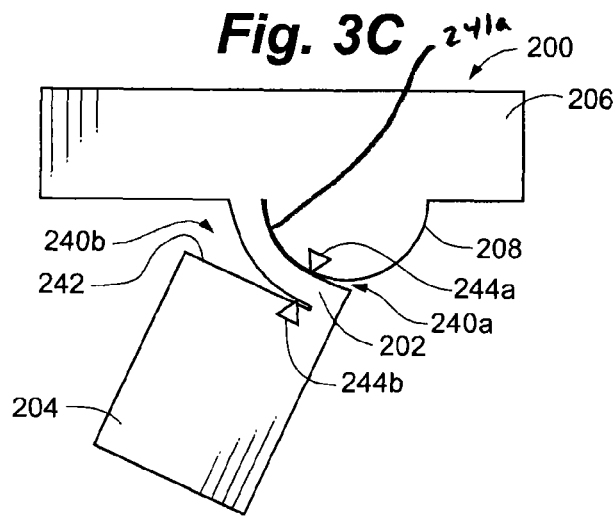

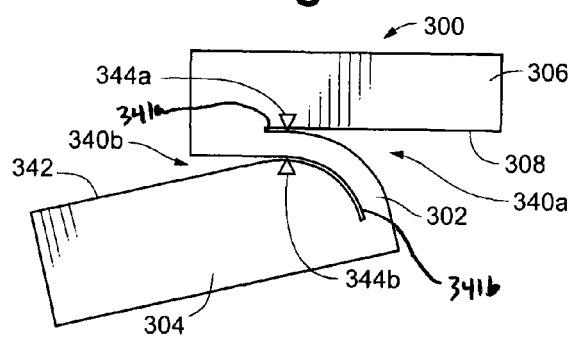
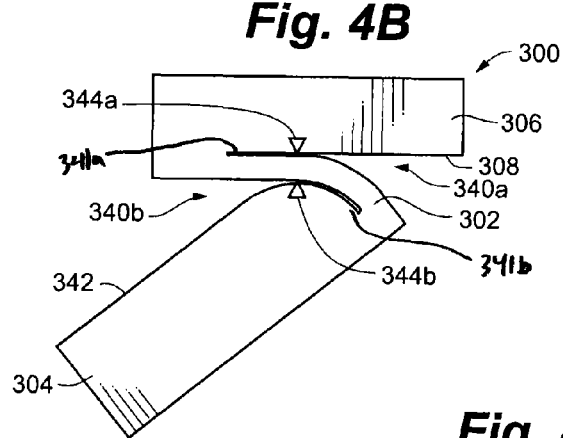
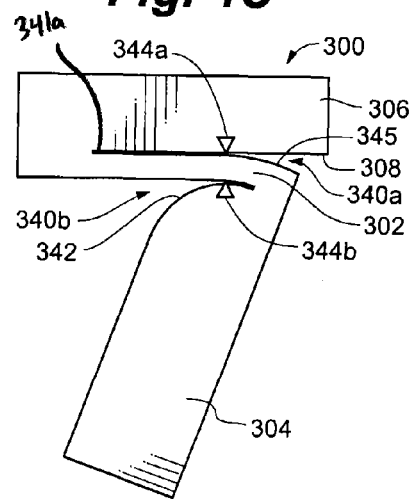

FLEXIBLE JOINT ARRANGEMENT INCORPORATING FLEXURE MEMBERS

PRIORITY

The present application claims the benefit of U.S. Provisional Application No. 61/142,104, filed Dec. 31, 2008 and U.S. Provisional Application No. 61/291,203, filed Dec. 30, 2009, each of which is incorporated herein in its entirety by reference.

FIELD OF THE INVENTION

The present invention relates to joint or linkage arrangements. More particularly, the present invention relates to a flexible joint arrangement including at least one flexure member that interfaces with wrapping surfaces defined on the bases to which the ends of the flexure member are connected.

BACKGROUND OF THE INVENTION

Many devices use joint arrangements to move one part of a device relative to another part of the device, such as moving between a collapsed configuration and an expanded configuration, rotating from one position to another, or performing more complicated manipulations. Joint arrangements can be designed to repeatedly move among configurations or positions, either for an infinite number of cycles or a finite number of cycles, or can be designed to move between configurations or positions only once or a limited number of times.

One approach for joint arrangements is to construct joints utilizing multiple parts where one part rotates relative to the other by means of sliding contact between components of the joint, such as a ball and socket or a pin and clevis. There are many known problems with such joints. Structures utilizing a plurality of multi-part joints can also suffer from a problem known as "dead band," in which movement at one end of the structure is not communicated to the other end until the intervening clearances in the multi-part joints are taken up. Such joints can also be difficult and expensive to manufacture to the required tolerances.

In view of these problems with rigid multi-part joints, joint arrangements comprised of straps, bands or leaf springs of flexible materials have been used, such as described in U.S. Pat. Nos. 3,386,128, 4,869,552, 5,133,108, 5,196,857 and 6,378,172. U.S. Pat. Nos. 6,175,989 and 6,772,479 describe flexible joint arrangements that utilize shape memory alloy materials. A resilient joint is disclosed in U.S. Pat. No. 7,435,032 that limits the maximum strain on the joint by connecting the ends of a flexure to cavities that limit the bend radius of the flexure to ensure that the maximum strain is not exceeded. The flexure member connects two separate structures and functions essentially like a standard leaf spring that stores the energy used to move it to the collapsed configuration in order to return to the expanded configuration.

One of the significant drawbacks of conventional designs for flexible joint arrangements is that such joints generally cannot support any significant loading in either compression or tension, and are therefore unsuitable for devices that must support such loads.

SUMMARY OF THE INVENTION

Flexible joint arrangements in accordance with various embodiments of the present invention employ at least one flexure member that interfaces with wrapping surfaces defined on the bases to which the ends of the flexure member are connected. The flexure members are configured to define a traveling instantaneous axis of rotation that moves along a path defined by the interface of the flexure and the wrapping surfaces as the bases are moved relative to each other. In one embodiment, the flexure members and the bases are constructed of a monolithic material. In another embodiment, the wrapping surfaces of the bases are asymmetric in cross-sectional shape. In other embodiments, the radius of curvature of the traveling instantaneous axis of rotation is configured to change only in discrete quantum steps without reversals. In still other embodiments, the flexible joint arrangement can be configured as one or more three bar linkages in which the middle bar is relatively rigid and the outer bars are flexure members in accordance with the various embodiments.

In an embodiment, a flexible joint arrangement includes a base, a structural member, and a flexure member connecting the structural member to the base that can comprise a one-piece unitary monolithic body. The flexure member can rotate to allow movement of the structural member relative to the base between a compressed configuration and an expanded configuration. The base and/or the structural member can define a surface referred to as a wrapping surface that provides a guide for rotation and/or wrapping of the flexure member as the structural member is moved relative to the base from the compressed configuration to the expanded configuration. In various embodiments, the wrapping surface can be concave, convex, or flat.

In another embodiment, a flexible joint arrangement includes a top base and a bottom base. A structural member is disposed intermediate the top base and bottom base and a flexure member connects each end of the structural member to the bases. The flexure members are configured to rotate to expand the structural member to allow the top base and the bottom base to move between a collapsed configuration and an expanded configuration relative to each other. The flexure members can each define a traveling instantaneous axis of rotation that moves along the interface of the flexure member and the wrapping surfaces as the top base and bottom base are moved between the collapsed configuration and the expanded configuration such that the axes of rotation travel at different heights within a plane transverse to the axes of rotation.

The thickness of the flexure in relation to the bend radius of the wrapping surface determines the fatigue life of the flexure due to movement. In some embodiments, flexures can be configured and designed to have very long fatigue life. In other embodiments, flexures can be configured and designed to have a finite fatigue life associated with a predetermined range of maximum number of cycles of expansion and contraction.

The above summary of various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE DRAWINGS

The invention may be more completely understood in consideration of the following detailed description of various embodiments of the invention in connection with the accompanying drawings, in which:

FIG. 2B is a partial side view of the flexible joint arrangement of FIG. 2A.

FIG. 2C is a partial side view of the flexible joint arrangement of FIG. 2A.

FIG. 3A is a partial side view of a flexible joint arrangement according to an embodiment of the present invention.

FIG. 3B is a partial side view of the flexible joint arrangement of FIG. 3A.

FIG. 3C is a partial side view of the flexible joint arrangement of FIG. 3A.

FIG. 4A is a partial side view of a flexible joint arrangement according to an embodiment of the present invention.

FIG. 4B is a partial side view of the flexible joint arrangement of FIG. 4A.

FIG. 4C is a partial side view of the flexible joint arrangement of FIG. 4A.

Figure 1:
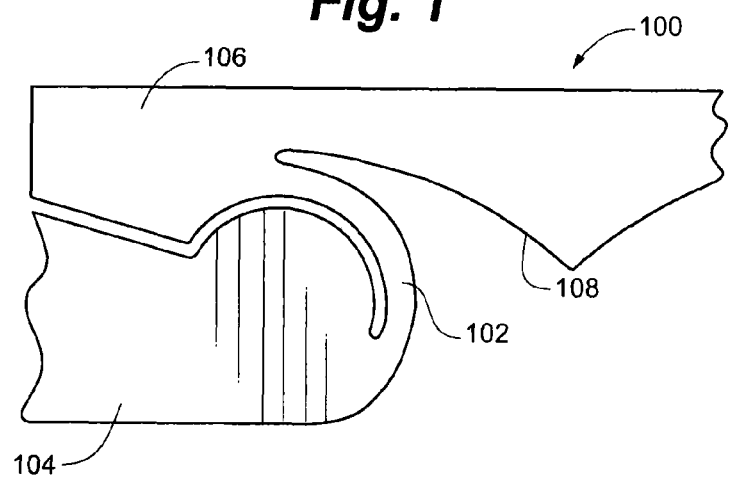
FIG. 1 is a partial side view of a flexible joint arrangement according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the various embodiments of the present invention.

Figure 9:
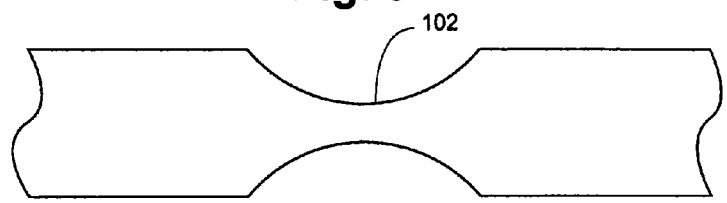
FIG. 9 is a side view of a circular flexure.
Figure 10:
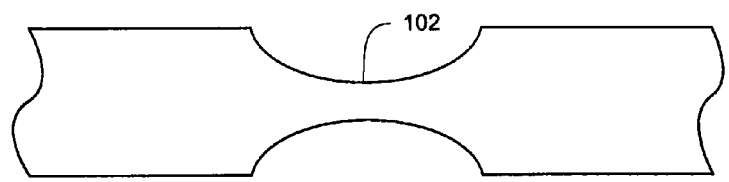
FIG. 10 is a side view of an elliptical flexure.
Figure 11:
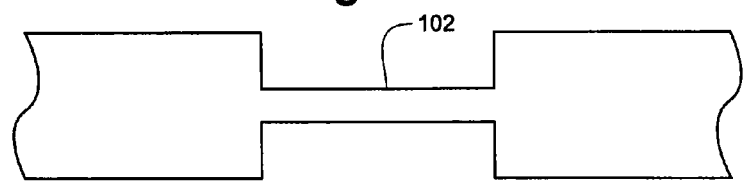
FIG. 11 is a side view of a leaf flexure.

Referring to FIG. 1, there can be seen a flexure joint or linkage 100 according to an embodiment of the present invention. Flexure linkage 100 includes a flexure member 102 connecting a structural member 104 to a base 106. A flexure member 102 is a thin, generally planar strip of material that allows movement of the structural member 104 relative to the base 106 and can support loading on the linkage 100. Structural member 104, base 106, and flexure member 102 can comprise a one piece unitary monolithic body. Flexure member 102 allows a one piece linkage 100 to behave similarly to a device having multiple parts and a rotating pin joint. Flexure members 102 can, for example, be band flexures (FIGS. 1, 2A-2C, 3A-3C and 4A-4C), circular flexures (FIG. 9), ellip-tical flexures (FIG. 10), or leaf flexures (FIG. 11). Additionally, such flexures 102 can taper along their length or can have a curved cross-section.

Base 104 can provide a wrapping surface 108 that guides the rotation of flexure member 102 as the structural member 104 and base 106 are moved relative to each other and can provide support to flexure member 102 under loading conditions. A wrapping surface 108 can be defined as a surface that sets the radius of curvature of the flexure throughout a discrete portion of the rotation of the flexure. In the depicted embodiment, the wrapping surface 108 is shown as concave, or inwardly curved.

Figure 2A:
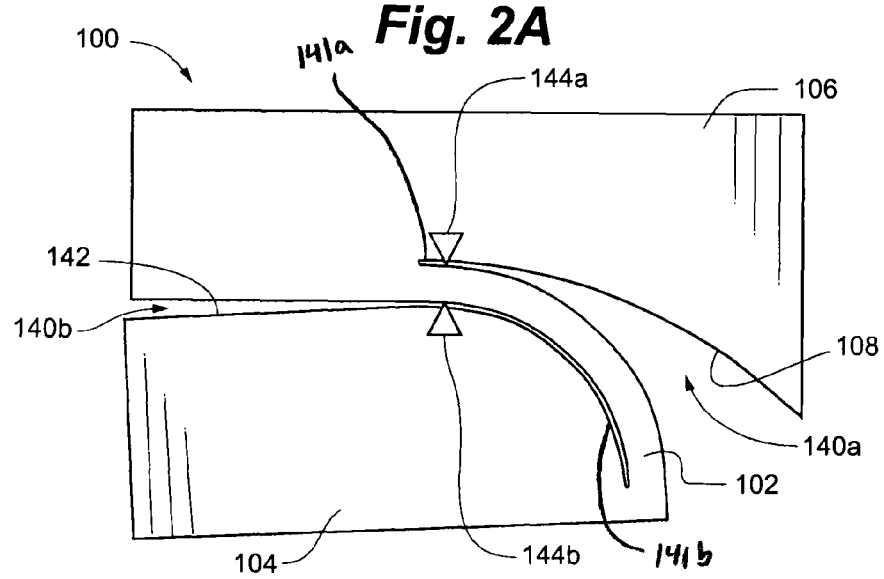
FIG. 2A is a partial side view of a flexible joint arrangement according to an embodiment of the present invention.

FIGS. 2A-2C depict the behavior of flexure member 102 as the structural member 104 is expanded relative to the base 106. Flexure member 102 defines a first open area, or kerf 140a, between wrapping surface 108 and flexure member 102 and a second kerf 140b between inner perimeter 142 of structural member 104 and flexure member 102. When the structural member 104 is in a collapsed configuration relative to base 106, kerf 140a is wider than kerf 140b. As the structural member 104 is expanded from base 106, flexure member 102 flattens out as guided by wrapping surface 108, so kerf 140b widens as kerf 140a narrows. The fulcrum or axis of rotation around which flexure member 102 bends is shown by arrows 144a and 144b. The fulcrum 144a, 144b translates along the flexure member 102 as it bends thereby defining a traveling instantaneous axis of rotation. Fulcrum 144a, 144b therefore travels in both vertical and horizontal directions. This provides for increased expansion of the structural member 104 relative to the base 106. As the fulcrum 144a, 144b moves along the flexure member 102, a greater portion of any compressive load on the linkage 100 is supported by the structural member 104 and, accordingly, the tensile forces on the flexure member 102 are reduced. The linkage 100 of this embodiment is therefore strongest when the structural member 104 is expanded to its fullest extent relative to the base 104 such that the load is normal to the wrapping surface.

As can be seen in FIGS. 2A-2C, the inner perimeter 142 of structural member 104 also acts as a wrapping surface for the flexure 102 (and the structural member 104 could be considered a second base). The wrapping surface of the inner perimeter 142 and the wrapping surface 108 are asymmetrical to each other. Having two asymmetrical wrapping surfaces provides a joint that is better in compression and optimizes load carrying capability. As the flexure 102 rotates, the radius of curvature at any given point on the flexure 102 is defined by either an interface 141b between the inner perimeter wrapping surface 142 and the flexure 102 or an interface 141a between the wrapping surface 108 and the flexure 102. To the left of the fulcrum 144a, 144b, the radius of curvature is defined by a path defined by the interface 141a between the wrapping surface 108 and the flexure 102. To the right of the fulcrum 144a, 144b, the radius of curvature is defined by a path defined by the interface 141b between the inner perimeter 142 and the flexure 102. Thus, throughout its rotation each point on the flexure 102 can have only two or a limited number of discrete different radii of curvature, i.e., discrete quantum steps of radii of curvature. This is in contrast to the flexure joints described in U.S. Pat. No. 7,435,032, for example, where the flexure member acts like a leaf spring and has a continually changing radius of curvature through a predetermined range as the joint is rotated. In addition, the two radiuses of curvature that the flexure 102 can undergo are a matter of degree; they do not transition between a positive curvature and a negative curvature so as to undergo a reversal of radius of curvature, which thereby reduces the strain on the flexure.

In an embodiment of a flexure linkage 200 shown in FIGS. 3A-3B, base 204 provides a wrapping surface 208 for flexure members 202 that is outwardly curved (in contrast to the inwardly curved wrapping surfaces 108 depicted in FIGS. 1 and 2A-2C). Flexure 202 curves around wrapping surface 208 as structural member 204 is expanded relative to base 206. In the collapsed state shown in FIG. 3A, flexure member 202 is parallel to an inner surface wrapping surface 242 of structural member 204. As the structural member 204 is expanded relative to base 206, flexure member 202 bends around wrapping surface 208, widening kerf 240b and narrowing kerf 240a. As shown by arrows 244a, 244b, the fulcrum or instantaneous axis of rotation translates along the length of flexure member 202 (in both the horizontal and vertical directions) as the device distracts. Fulcrum 244a, 244b is always perpendicular to inner surface 242 of structural member 204. This results in the entirety of a load on the linkage 200 being carried in compression by the structural member 204. Therefore, there is no tensile force on flexure member 202. This allows flexure member 202 to be easily sized to enjoy an essentially infinite fatigue life. This embodiment allows a linkage to be constructed from a material, such as nitinol, that provides strong compressive support when it is of large dimensions but that distorts easily when slender members of the same material are under tension or bending. Similar to flexure member 102, points along the flexure member 202 to the left of the fulcrum 244a, 244b define a path having a radius of curvature defined by an interface 241a between wrapping surface 208 and the flexure 202 and points to the right of fulcrum 244a, 244b define a path having a radius of curvature defined by an interface 241b between the inner perimeter wrapping surface 242 and the flexure 202 as the flexure member 202 rotates.

FIGS. 4A-4C depict a further embodiment of a flexure linkage 300. Wrapping surface 308 on base 306 is flat. Flexure member 302 begins curved around inner surface 342 of structural member 304 and flattens out, thereby widening kerf 340b and narrowing kerf 340a, as the device distracts. Fulcrum 344a, 344b or instantaneous axis of rotation again translates along flexure member 302 as the structural member 304 is expanded relative to base 306, providing increased expansion. As the structural member 304 is expanded relative to base 306, structural member 304 supports more of any load on linkage 300 in compression and less is supported by the flexure member 302 in tension. Points along the flexure member 302 to the left of the fulcrum 344a, 344b define a path having a radius of curvature defined by an interface 341a between the wrapping surface 308 and the flexure 302 while points to the right of the fulcrum 344a, 344b define a path having a radius of curvature defined by an interface between the inner perimeter wrapping surface 342 and the flexure 302.

As depicted in the above figures, when the structural member is fully expanded relative to the base, the flexure member can at least partially rest against wrapping surface of base. Thus, any compressive load on structural member may be partially supported by base during transition or can completely rest on 345 with no load on flexure. Alternatively, a linkage can be configured such that no portion of the flexure rests on the base, so the entirety of any load on the linkage will be carried by the flexure.

The thickness of the flexure in relation to the bend radius of the wrapping surface determines the fatigue life of the flexure due to movement. In some embodiments, flexures can be configured and designed to have very long fatigue life. In one embodiment, a device made from nitinol having a thickness of the flexure members that is preferably between 8% and 10% of the bend radius of the wrapping surface, with a maximum thickness of 18% has an infinite fatigue life. In another embodiment, a flexure made from PEEK preferably has a thickness that is 4.5% to 6.4% of the bend radius, with a maximum thickness of 15%. In a further embodiment, a flexure comprised of annealed titanium can have a thickness of up to 18% of the bend radius. In other embodiments, flexures can be configured and designed to have a finite fatigue life associated with a predetermined range of maximum number of cycles of expansion and contraction.

Flexures can exhibit either plasticity, defined as permanent deformation, or elasticity, essentially infinite life. Flexures will exhibit plasticity if the ratio of the flexure thickness to the bend radius exceeds the percent elongation before yield of the material comprising the flexure. Flexures will exhibit elasticity if the ratio of the flexure thickness to the bend radius is less than the percent elongation before yield of the material. Where flexures operate elastically, they can be used in devices requiring repeated repositioning. If flexures are configured to operate plastically, they can support loading of increased magnitude indefinitely, but should be left at a predetermined position and not repositioned more than a limited number of times.

Figure 5:
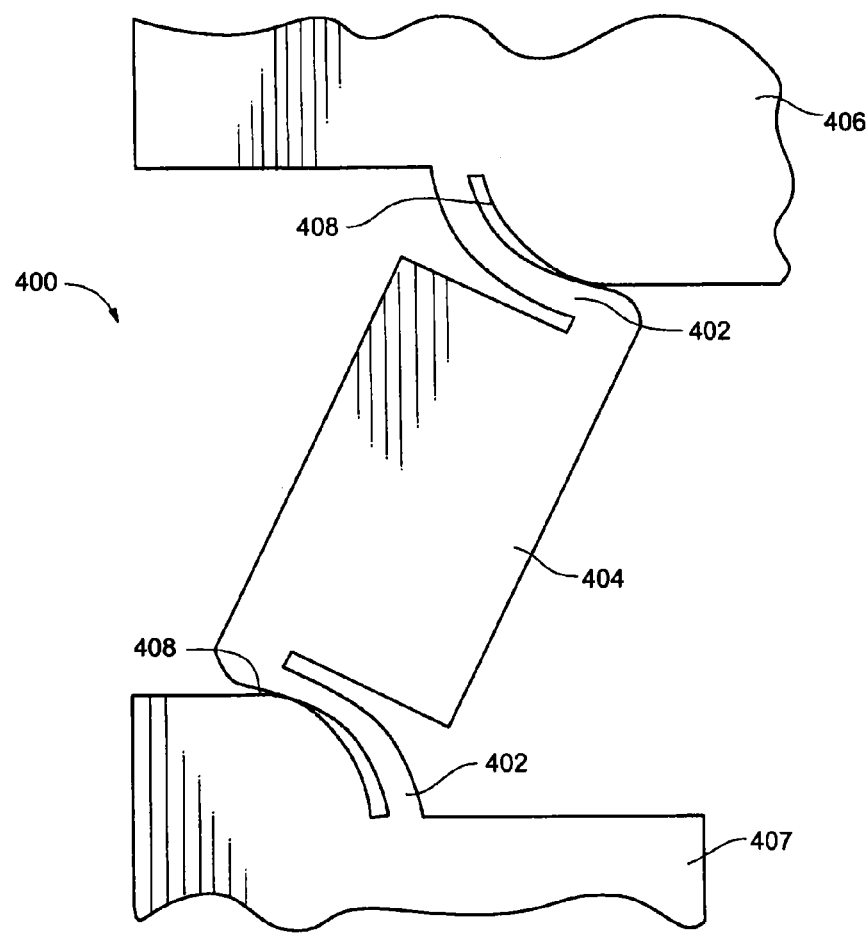
FIG. 5 is a partial side view of a flexible joint arrangement according to an embodiment of the present invention.
Figure 6A:
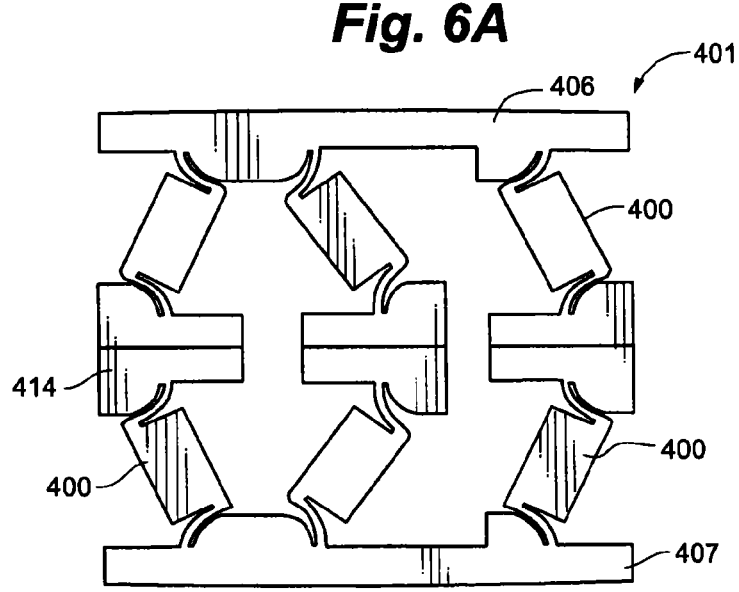
FIG. 6A is a side view of a device employing a plurality of flexible joint arrangements according to an embodiment of the present invention.
Figure 6B:
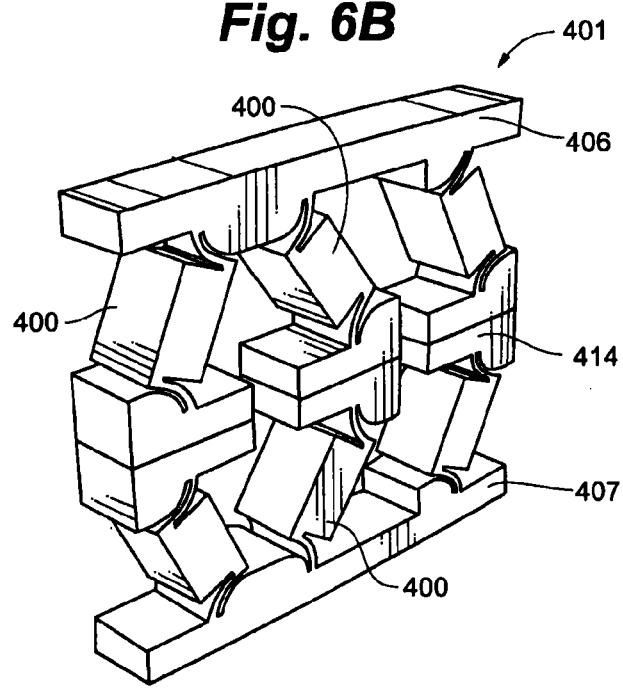
FIG. 6B is a perspective view of the device of FIG. 6A.
Figure 7A:
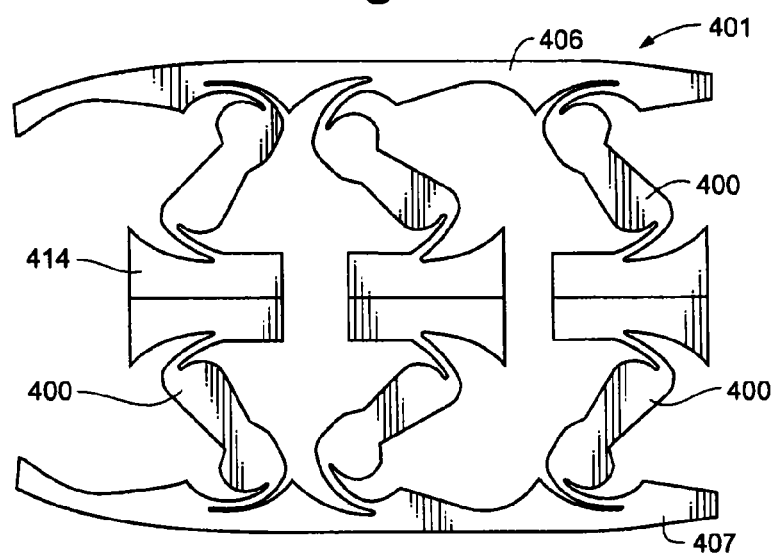
FIG. 7A is a side view of a device employing a plurality of flexible joint arrangements according to an embodiment of the present invention.
Figure 7B:
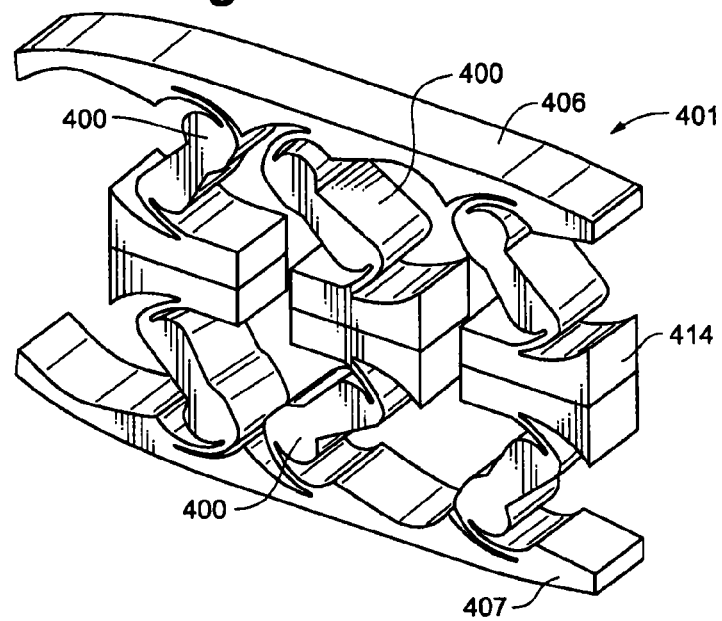
FIG. 7B is a perspective view of the device of FIG. 7A.

Referring to FIG. 5, a flexure linkage 400 according to an embodiment of the present invention can include a flexure member 402 positioned at each end of a structural member 404 connecting the structural member 404 to a top base 406 and a bottom base 407. This configuration essentially comprises a three bar linkage between the bases 406, 407, with the end bars (the flexure members 402) being flexible and the middle bar (the structural member 404) being rigid. Flexure linkage 400 can be used to distract top base 406 and bottom base 407 relative to each other. Flexure linkage 400 therefore includes two instantaneous axes of rotation that move along each flexure 402 as described above with reference to the fulcrum along which the flexure members bend as the linkage expands. The two axes of rotation are mirror images of each other and travel at different heights in the same plane that is transverse to the axes. Although flexure linkage 400 is depicted as having outwardly curved wrapping surfaces 408, such a flexure linkage 400 employing a flexure member 402 on each end could include wrapping surfaces of any other configuration. In some embodiments, wrapping surface 408 on top base 406 and wrapping surface 408 on bottom base 407 can have different geometries.

Figure 8A:
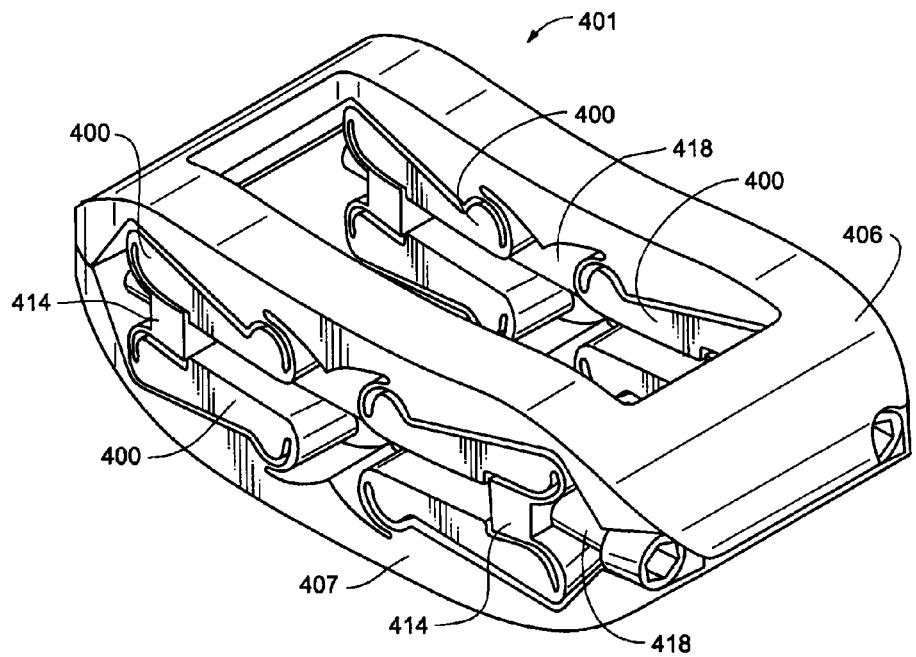
FIG. 8A is a perspective view of a device employing a plurality of flexible joint arrangements according to an embodiment of the present invention.
Figure 8B:
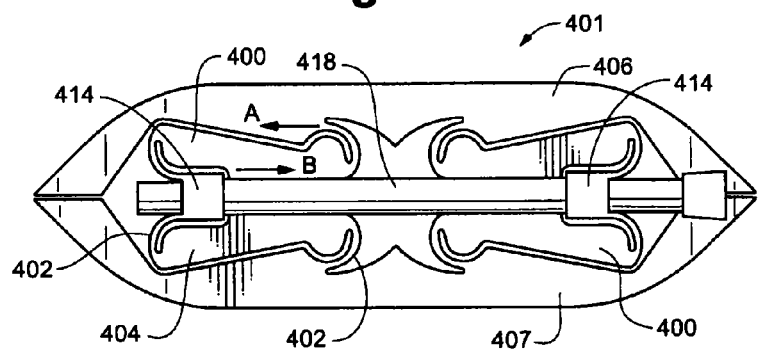
FIG. 8B is a side view of the device of FIG. 8A.

As can be seen in FIGS. 6A-6B and 7A-7B, a device 401 can include multiple flexure linkages 400. Flexure linkages 400 can be connected vertically between bases 406, 407 and/or aligned in a row lengthwise along bases 406, 407. Flexure linkages 400 can also situated side-by-side across a width of bases 406, 407 as shown in FIGS. 8A and 8B. Such devices 401 can include blocks 414 acting as common bases for vertically adjacent flexure linkages 400. Blocks 414 can be tapped to accommodate an expansion mechanism, such as a drive screw 418 (FIGS. 8A and 8B) that can be used to expand flexure linkages 400 and distract bases 406, 407.

Unlike many common scissor jacks, such as, for example, car jacks, device 401 can easily be distracted from its lowest, or most compressed, state. This is because the flexure members 402 on each end of a given structural member 404 are oriented such that the tensile loads on the flexure members 402 do not act towards each other, but instead pass by each other, like passing cars (see arrow A and arrow B in FIG. 8B). Common jacks, which do not utilize flexure members, may have difficulty distracting from the lowest state because the tensile loads can act "heads on" with each other, putting the device under strong internal horizontal compression but without a significant force component in the vertical direction at the lowest state that can easily initiate distraction. The tension in the flexure member required to support a compressive load is equal to the compressive load multiplied by the cosine of the angle of the rigid link divided by the sine of the rigid link. Because the sine of zero degrees, the angular position of normal scissor jacks in the compressed state, is equal to zero, the force required for initial distraction can be effectively very large. The rigid links of the device of various embodiments of the present invention may start off in the position of zero angular position, but because the flexure members are on opposing sides of the rigid links the effective angular position is non-zero, making the force required for initial distraction finite and generally smaller than a conventional scissor jack.

Although flexure members have been described herein as being generally planar, flexure members can have various other shapes. For example, flexure members could have an arcuate configuration. Flexure members could also include lips or ridges projecting upwardly from one or more surfaces. Additionally, flexure members could be curved along their width, creating a singularity or bias that could cause them to have a position, or positions, in which they are inclined to reside throughout the normal range of motion.

In some embodiments, flexible joint arrangements and devices employing flexible joint arrangements according to embodiments of the present invention can comprise a one-piece unitary body. This provides great cost savings over devices that require multiple pieces to be separately manufactured and assembled. In one embodiment, the device can be manufactured using wire or sink edm. In another embodiment, the device can be manufactured using three-dimensional printing techniques or the like. In some embodiments, portions of the flexible joint arrangements and devices, such as the flexure members, blocks and backstops, for example, can be machined separately and welded or otherwise attached to the device.

Flexible joint arrangements as disclosed herein and devices utilizing flexible joint arrangements can be constructed in various sizes, including, macro, micro, and nano sized applications.

In one embodiment, flexures on a macro scale may be made of a different material or made with a different material treatment than the rest of the structure and then affixed in position with welding, adhesives, or mechanical fasteners. In some embodiments, the flexures may be configured in a nesting geometry. The material from which the flexures are made could be cold rolled to improve its fatigue properties and then installed in the device.

In another embodiment, flexures on a macro scale could be laminated beams with a core of a stiff material, a softer material, or no material. Such lamination and material variation through the flexure itself would lead to precise control over the strength and fatigue properties of the flexures and the device employing the flexures. Specifically, a laminated beam having a soft core or no core at all would allow the flexure to get thinner as it bent further around the support structure, maintaining the operation of the flexure in the elastic region of the material from which it is made.

In another embodiment, in a device on a macro scale the surfaces against which the flexures roll could be machined and affixed such that the effective kerf at the instantaneous centers of rotation is effectively zero in the unloaded state. This would be advantageous because it would minimize the local stresses with the flexure and the structure, resulting in a stronger device, capable of greater fatigue life.

Flexures on a macro scale could also be layered with the same or different materials such that if one layer were to crack, the crack would not propagate through to the next layer.

On a micro scale, flexures could be manufactured with a layering process that would allow for different levels of the flexure to be doped with different materials enhancing the strength or fatigue properties of the flexure at different levels. For example, if sintering were used, Ti 6A1 4V Standard could be used for the main body of the flexure, while Ti 6A1 4V ELI could be used to create surface features given that the standard form of titanium has improved smooth fatigue properties and the ELI form of titanium has improved notched fatigue properties.

On the nano scale, many similar doping or material manipulation properties would also be available. Additionally ion intercalation could be used to move the blocks closer together or farther apart, resulting in what could be a chemically actuated device, sensor, or valve.

In all scales, the flexure itself could be replicated, mirrored, multiplexed, rotated, extruded, or revolved to create further novel structures or flexures.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, etc. have been described for use with disclosed embodiments, others besides those disclosed may be utilized without exceeding the scope of the invention.

The invention claimed is:

1. A flexible joint comprising:
a top base comprising a lower surface;
a bottom base comprising an upper surface; and
a plurality of flexure assemblies disposed between and unitarily formed with the top and bottom bases, each flexure assembly comprising:
an intermediate block comprising opposing upper and lower surfaces;
upper and lower structural members each disposed between the intermediate block and a respective one of the top and bottom bases, each structural member including opposing upper and lower surfaces and opposing side surfaces;
a flexure member disposed on each opposing upper and lower surface of each structural member, the flexure members connecting each structural member to a respective one of the upper and lower surfaces of the intermediate block and to a respective lower or upper surface of one of the top and bottom bases;
wherein the opposing upper and lower surfaces of the structural members, the upper and lower surfaces of the intermediate block, the lower surface of the top base, and the upper surface of the bottom base each comprise a wrapping surface adjacent a corresponding flexure member, and wherein the wrapping surfaces of the top base, bottom base, and intermediate block define an arcuate curve;
wherein each structural member is rotatable with respect to the top and bottom bases to move the top base relative to the bottom base, such that the top base and the bottom base are movable between a compressed configuration and an expanded configuration relative to each other, the compressed configuration characterized by:
the top and bottom bases being moved toward each other such that the wrapping surfaces of each structural member are aligned with a side surface of a respective flexure member so that the flexure members conform to the shape of the wrapping surfaces of the structural member, and one of the opposing side surfaces of each structural member is shaped to correspondingly engage one of the respective upper or lower surfaces of the top and bottom bases; and the expanded configuration characterized by:
the top and bottom bases being displaced from each other such that the arcuate wrapping surfaces of each of the top base, bottom base, and the opposing upper and lower surfaces of the intermediate block are engaged with an opposing side surface of a respective one of the flexure members so that the flexure members conform to the shape of the arcuate wrapping surfaces.

2. The flexible joint of claim 1, wherein the arcuate wrapping surfaces of the top base and the bottom base provide a guide for rotation of the flexure members and define a radius of curvature of at least a portion of the flexure members as the top base and bottom base are moved relative to each other, wherein the wrapping surfaces provide a guide for rotation of the flexure members by interfacing with the flexure members as they rotate.

3. The flexible joint of claim 2, wherein the arcuate wrapping surfaces have either a concave or convex cross-sectional shape.

4. The flexible joint of claim 1, wherein the flexure members are selected from the group consisting of: a band flexure, a circular flexure, an elliptical flexure and a leaf flexure.

5. The flexible joint of claim 1, wherein the arcuate wrapping surfaces of the top base and the bottom base each have a geometry that is different from a geometry of the other wrapping surface.

6. The flexible joint of claim 2, wherein the interfacing of the arcuate wrapping surfaces with the flexure members results in translational movement of the structural members.

* * * * *